(12) United States Patent
Livak et al.

(10) Patent No.: US 6,821,727 B1
(45) Date of Patent: Nov. 23, 2004

(54) HYBRIDIZATION ASSAY USING SELF-QUENCHING FLUORESCENCE PROBE

(75) Inventors: Kenneth J. Livak, San Jose, CA (US); Susan J. A. Flood, Fremont, CA (US); Jeffrey Mamoro, Aurora, CO (US); Khairuzzaman Bashar Mullah, Union City, CA (US)

(73) Assignee: Applera Corporation, Foster City, CA (US)

(*) Notice: Subject to any disclaimer, the term of this patent is extended or adjusted under 35 U.S.C. 154(b) by 0 days.

(21) Appl. No.: 09/627,753

(22) Filed: Jul. 28, 2000

Related U.S. Application Data

(63) Continuation of application No. 09/436,454, filed on Nov. 8, 1999, now Pat. No. 6,258,569, which is a continuation of application No. 09/207,170, filed on Dec. 7, 1998, now Pat. No. 6,030,787, which is a continuation of application No. 08/558,303, filed on Nov. 15, 1993, now Pat. No. 5,876,930, which is a continuation-in-part of application No. 08/340,558, filed on Nov. 16, 1994, now Pat. No. 5,538,848.

(51) Int. Cl.$^7$ .......................... C12Q 1/68; C12P 19/34; C07H 19/00; C07H 21/00; C07H 21/02
(52) U.S. Cl. .................. 435/6; 435/91.1; 435/91.2; 536/22.1; 536/23.1; 536/24.3; 536/24.32; 536/23.33; 536/25.3; 536/25.32; 536/26.6
(58) Field of Search .................. 435/6, 91.1, 91.2; 536/22.1, 23.1, 24.3, 24.32, 24.33, 25.3, 25.32, 26.6

(56) References Cited

U.S. PATENT DOCUMENTS

| | | | |
|---|---|---|---|
| 4,220,450 A | 9/1980 | Maggio | 23/230 |
| 4,775,619 A | * 10/1988 | Urdea | 435/6 |

(List continued on next page.)

FOREIGN PATENT DOCUMENTS

| | | | |
|---|---|---|---|
| AI | 640089 | | 8/1993 |
| EP | 0229943 | * | 7/1987 |
| EP | 0232967 A | | 8/1987 |

(List continued on next page.)

OTHER PUBLICATIONS

Livak et al. "Oligonucleotides with fluorescent dyes at opposite ends provide a quenched probe system useful for detecting PCR product and nucleic acid hybridization" PCR Methods and Applications, vol. 4, pp. 357–362, 1995.*

(List continued on next page.)

*Primary Examiner*—Jezia Riley
(74) *Attorney, Agent, or Firm*—David J Weitz; Vincent M Powers

(57) ABSTRACT

A hybridization assay is provided which uses an oligonucleotide probe which includes a fluorescent reporter molecule and a quencher molecule capable of quenching the fluorescence of the reporter molecule. The oligonucleotide probe is constructed such that the probe exists in at least one single-stranded confirmation when unhybridized where the quencher molecule is near enough to the reporter molecule to quench the fluorescence of the reporter molecule. The oligonucleotide probe also exists in at least one conformation when hybridized to a target polynucleotide where the quencher molecule is not positioned close enough to the reporter molecule to quench the fluorescence of the reporter molecule. By adopting these hybridized and unhybridized conformations, the reporter molecule and quencher molecule on the probe exhibits different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence until the probe is either hybridized or digested.

2 Claims, 2 Drawing Sheets

U.S. PATENT DOCUMENTS

| | | | |
|---|---|---|---|
| 4,996,143 A | 2/1991 | Heller et al. | 435/6 |
| 5,210,015 A | 5/1993 | Gelfand et al. | 435/6 |
| 5,332,659 A | 7/1994 | Kidwell | 435/6 |
| 5,487,972 A | 1/1996 | Gelfand et al. | 435/6 |
| 5,491,063 A | 2/1996 | Fisher et al. | 435/6 |
| 5,538,848 A | 7/1996 | Livak et al. | 435/5 |
| 5,565,554 A | 10/1996 | Glazer et al. | 536/26.6 |
| 5,607,834 A | 3/1997 | Bagwell | 435/6 |
| 5,654,419 A | 8/1997 | Mathies | 536/25.4 |
| 5,688,648 A | 11/1997 | Mathies et al. | 435/6 |
| 5,723,591 A | 3/1998 | Livak et al. | 536/22.1 |
| 5,763,181 A | 6/1998 | Han et al. | 435/6 |
| 5,804,375 A | 9/1998 | Gelfand et al. | 436/6 |
| 5,876,930 A * | 3/1999 | Livak et al. | 435/6 |
| 5,925,517 A | 7/1999 | Tyagi et al. | 435/6 |
| 6,008,373 A | 12/1999 | Waggoner | 548/427 |
| 6,030,787 A * | 2/2000 | Livak et al. | 435/6 |

FOREIGN PATENT DOCUMENTS

| | | | |
|---|---|---|---|
| EP | 0343955 A | | 5/1988 |
| EP | 0420102 A | | 4/1991 |
| EP | 0457213 A | | 11/1991 |
| EP | 0 523 557 B1 | | 7/1992 |
| EP | 0523557 A | | 1/1993 |
| EP | 0601889 | * | 6/1994 |
| JP | 5123195 | | 5/1993 |
| WO | WO 90/03446 | | 4/1990 |
| WO | WO 92/02638 | | 2/1992 |
| WO | WO 93/13224 | | 7/1993 |
| WO | WO 95/03429 | | 2/1995 |
| WO | WO 95/21266 | | 8/1995 |
| WO | WO 96/30540 | | 10/1996 |

OTHER PUBLICATIONS

Lee et al. "Allelic discrimination by nick–translation PCR with fluorogenic probes" Nucleic acids research, 21, pp. 3761–3766, 1993.*

Bagwell et al., "A new homogeneous assay system for specific nucleic acid sequences: poly–dA and poly–A detection," Nucleic Acids Research, vol. 22 No. 12, pp. 2424–2425 (1994).

Lyamichev et al., "Structure–Specific Endonucleolytic Cleavage of Nucleci Acids by Eubacterial DNA Polymerases," Science, vol. 260, pp. 778–783, May 7, 1993.

Lee et al., "Characterization of $Mg^{2+}$–Dependent 3'–Processing Activity for Human Immunodeficiency Virus Type 1 Integrase in Vitro: Real–Time Kinetic Studies Using Fluorescence Resonance Energy Transfer," *Biochemistry*, vol. 34, No. 32, pp. 10205–10214 (1995).

Lee et al., "Fluorescence Assays for DNA Cleavage," *Methods in Enzymology*, vol. 278, pp. 343–363 (1997).

Search Report of WO 96/15270 by Livak, (PCT/US95/14882).

Database WPI, Sect. Ch., Wk. 8608, Derwent Publ. Ltd., London, GB Jan. 1986, JP 5015439 (1993) "Determine Polynucleotide Single Strand Label Luminous Polynucleotide Substance".

Agrawal and Zamecnik, "Site Specifice Functionalization of Oligonucleotides for Attaching Two Different Reporter Groups," Nucl. Acids Res. 18(18) :5419–5423 (1990).

Cardullo et al., "Detection of Nucleic Acid Hybridization by Nonradiative Fluorescence Resonance Energy Transfer," Proc. Natl. Acad. Sci. USA 85:8790–8794 (1988).

Clegg, "Fluorescence Resonance Energy Transfer and Nucleic Acids," Methods of Enzymology 211:353–389 (1992).

Clegg et al., "Observing the Helical Geoometry of Double–Stranded DNA in Solution by Fluorescence Resonance Energy Transfer," Proc. Natl. Acad. Sci. USA 90:2994–2998 (1993).

Guo et al., "Direct Fluores. Analy. of Genetic Polymor. by Hybrid. with oligonucl. arrays on glass supports," Nucl. Acids Res., 22(24):5456–5465 (1994).

Heller et al., "Fluorescent Energy Transfer Oligonucleotide Probes," Abstract 248, Feb. Proc. 46:1968 (1987).

Higuchi et al., "Simultaneous Amplification and Detection of Specific DNA Sequences," Biotechnology 10:413–417 (1992).

Higuchi et al., "Kinetic PCR Analysis: Real–Time Monitoring of DNA Amplification Reactions," Biotechnology 11:1026–1030 (1993).

Holland et al., "Detection of Specific Polymerase Chain Reaction Product by Utilizing the 5'–3' Exonuclease Activity of Thermus aquaticus DNA Polymerase," Proc. Natl. Acad. Sci. USA 88:7276–7280 (1991).

Ju et al., "Design and Synthesis of Fluorescence Energy Transfer Dye–Labeled Primers and their Application for DNA Sequencing and Analysis," Anal. Biochem. 231:131–140 (1995).

Lee et al., "DNA sequencing with dye–labeled terminators and T7 DNA polymerase: effect of dyes and dNTPs on incorporation of dye–terminators and probability analysis of termination fragments," Nucl. Acids Res. 20 (10) : 2471–2483 (1992).

Mergny et al., "Fluorescence Energy Transfer as a Probe for Nucleic Acid Structures and Sequences," Nucl. Acids Res. 22(6) :920–928 (1994).

Ozaki et al., "The estimation of distances between specific backbone–labeled sites in DNA using fluorescence resonance enrgy transfer," Nucl. Acids Res. 20(19) :5205–5214 (1992).

Parkhurst et al., "Kinetic Studies by fluorescence resonance energy transfer employing a double–labeled oligonucleotide: hybridization to the oligonucleotide complement and to single–stranded DNA," Biochemistry 34:285–292 (1995).

Parkhurst & Parkhurst, "Donor–Acceptor Distance Distributions in a Double–Labeled Fluorescnet Oligonucleotide Both as a Single Strand and in Duplexes," Biochemistry 34:293–300 (1995).

Parkhurst & Parkhurst, "Changes in the end–to–end distance distribution in an oligonucleotide following hybridization," Time–Resolved Laser Spectroscopy in Biochemistry (Ladkowicz, J.R. Ed.), Proc SPIE 2137:475–485 (1994).

Parkhurst & Parkhurst, "Kinetic Studies of Oligonucleotide–DNA Hybridization in Solution by Fluorescence Resonance Energy Transfer," Abstr. Biophys. J. 64:A266 (1993).

Parkhurst & Parkhurst, "Fluorescence Studies of Oligonucleotide–DNA Hybridization in Solution and of Oligonucleotide End to End Distance Distributions," Abstracts, 11th International Congress on Photobiology, Kyoto, Japan, p. 258, Photobiology Association of Japan, Kyoto, Japan (1992).

Roche Inventor Disclosure disclosed to Applied Biosystems prior to Nov. (1994).

Stryer et al., "Energy Transfer: A Spectroscopid Ruler," Proc. Natl. Acad. Sci. USA 58:719–726 (1967).

Tyagi et al., Molecular Beacons: Probes that fluoresce upon hybridization, Nature Biotechnology 14:303–308 (1996).

Wu et al., "Resonance Energy Transfer: Methods and Applications," Anal. Biochem. 218:1–13 (1994).

* cited by examiner

FIG. 1

HYBRIDIZATION ASSAY USING SELF-QUENCHING FLUORESCENCE PROBE

RELATIONSHIP TO COPENDING APPLICATION

This application is a continuation of application Ser. No. 09/436,454 filed Nov. 8, 1999, now U.S. Pat. No. 6,258,569 which is a continuation of application Ser. No. 09/207,170, filed Dec. 7, 1998, now U.S. Pat. No. 6,030,787, which is a continuation of application Ser. No. 08/558,303, filed Nov. 15, 1995, now U.S. Pat. No. 5,876,930, which is a continuation-in-part of application Ser. No. 08/340,558, filed Nov. 16, 1994, now U.S. Pat. No. 5,538,848, which are all incorporated herein by reference.

BACKGROUND OF THE INVENTION

1. Field of the Invention

The invention relates generally to fluorescent probes which include a fluorescent reporter molecule and a fluorescent quencher molecule. More specifically, the invention relates to fluorescent probes which include a fluorescent reporter molecule and a fluorescent quencher molecule which may be used in hybridization assays and in nucleic acid amplification reactions, especially polymerase chain reactions (PCR).

2. Description of Related Art

Fluorescent reporter molecule—quencher molecule pairs have been incorporated onto oligonucleotide probes in order to monitor biological events based on the fluorescent reporter molecule and quencher molecule being separated or brought within a minimum quenching distance of each other. For example, probes have been developed where the intensity of the reporter molecule fluorescence increases due to the separation of the reporter molecule from the quencher molecule. Probes have also been developed which lose their fluorescence because the quencher molecule is brought into proximity with the reporter molecule. These reporter—quencher molecule pair probes have been used to monitor hybridization assays and nucleic acid amplification reactions, especially polymerase chain reactions (PCR), by monitoring either the appearance or disappearance of the fluorescence signal generated by the reporter molecule.

As used herein, a reporter molecule is a molecule capable of generating a fluorescence signal. A quencher molecule is a molecule capable of absorbing the fluorescence energy of an excited reporter molecule, thereby quenching the fluorescence signal that would otherwise be released from the excited reporter molecule. In order for a quencher molecule to quench an excited fluorophore, the quencher molecule must be within a minimum quenching distance of the excited reporter molecule at some time prior to the reporter molecule releasing the stored fluorescence energy.

Probes containing a reporter molecule—quencher molecule pair have been developed for hybridization assays where the probe forms a hairpin structure, i.e., where the probe hybridizes to itself to form a loop such that the quencher molecule is brought into proximity with the reporter molecule in the absence of a complementary nucleic acid sequence to prevent the formation of the hairpin structure. WO 90/03446; European Patent Application No. 0 601 889 A2. When a complementary target sequence is present, hybridization of the probe to the complementary target sequence disrupts the hairpin structure and causes the probe to adopt a confirmation where the quencher molecule is no longer close enough to the reporter molecule to quench the reporter molecule. As a result, the probes provide an increased fluorescent signal when hybridized to a target sequence than when unhybridized. Probes including a hairpin structure have the disadvantage that they can be difficult to design and may interfere with the hybridization of the probe to the target sequence.

Assays have also been developed for identifying the presence of a hairpin structure using two separate probes, one containing a reporter molecule and the other a quencher molecule. Mergney, et al., Nucleic Acids Research, 22:6 920–928 (1994). In these assays, the fluorescence signal of the reporter molecule decreases when hybridized to the target sequence due to the quencher molecule being brought into proximity with the reporter molecule.

One particularly important application for probes including a reporter—quencher molecule pair is their use in nucleic acid amplification reactions, such as polymerase chain reactions (PCR), to detect the presence and amplification of a target nucleic acid sequence. In general, nucleic acid amplification techniques have opened broad new approaches to genetic testing and DNA analysis. Amheim and Erlich, Ann. Rev. Biochem., 61: 131–156 (1992). PCR, in particular, has become a research tool of major importance with applications in, for example, cloning, analysis of genetic expression, DNA sequencing, genetic mapping and drug discovery. Amheim and Erlich, Ann. Rev. Biochem., 61: 131–156 (1992); Gilliland et al., Proc. Natl. Acad. Sci., 87: 2725–2729 (1990); Bevan et al., PCR Methods and Applications, 1: 222–228 (1992); Green et al., PCR Methods and Applications, 1: 77–90 (1991); Blackwell et al., Science, 250: 1104–1110 (1990).

The widespread applications of nucleic acid amplification techniques has driven the development of instrumentation for carrying out the amplification reactions under a variety of circumstances. Important design goals for such instrument development have included fine temperature control, minimization of sample-to-sample variability in multi-sample thermal cycling, automation of pre- and post-reaction processing steps, high speed temperature cycling, minimization of sample volumes, real time measurement of amplification products and minimization of cross contamination, for example, due to "sample carryover". In particular, the design of instruments permitting amplification to be carried out in closed reaction chambers and monitored in real time would be highly desirable for preventing cross-contamination. Higuchi et al., Biotechnology, 10: 413–417 (1992) and 11: 1026–1030 (1993); and Holland et al., Proc. Natl. Acad. Sci., 88: 7276–7280 (1991). Clearly, the successful realization of such a design goal would be especially desirable in the analysis of diagnostic samples, where a high frequency of false positives and false negatives, for example caused by "sample carryover", would severely reduce the value of an amplification procedure. Moreover, real time monitoring of an amplification reaction permits far more accurate quantification of C) starting target DNA concentrations in multiple-target amplifications, as the relative values of close concentrations can be resolved by taking into account the history of the relative concentration values during the reaction. Real time monitoring also permits the efficiency of the amplification reaction to be evaluated, which can indicate whether reaction inhibitors are present in a sample.

Holland et al., (cited above), U.S. Pat. No. 5,210,015 to Gelfand, et al., and others have proposed fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear.

The Taq-Man approach, illustrated in FIG. 1, uses an oligonucleotide probe containing a reporter molecule—quencher molecule pair that specifically anneals to a region of a target polynucleotide "downstream", i.e. in the direction of extension of primer binding sites. The reporter molecule and quencher molecule are positioned on the probe sufficiently close to each other such that whenever the reporter molecule is excited, the energy of the excited state nonradiatively transfers to the quencher molecule where it either dissipates nonradiatively or is emitted at a different emission frequency than that of the reporter molecule. During strand extension by a DNA polymerase, the probe anneals to the template where it is digested by the 5'→3' exonuclease activity of the polymerase. As a result of the probe being digested, the reporter molecule is effectively separated from the quencher molecule such that the quencher molecule is no longer close enough to the reporter molecule to quench the reporter molecule's fluorescence. Thus, as more and more probes are digested during amplification, the number of reporter molecules in solution increases, thus resulting in an increasing number of unquenched reporter molecules which produce a stronger and stronger fluorescent signal.

Three main factors influence the utility of reporter-quencher molecule pair probes in hybridization and amplification assays. The first factor is the effectiveness of the quencher molecule on the probe to quench the reporter molecule. This first factor, herein designated "$RQ^-$", can be characterized by the ratio of the fluorescent emissions of the reporter molecule to the quencher molecule when the probe is not hybridized to a complementary polynucleotide. That is, $RQ^-$ is the ratio of the fluorescent emissions of the reporter molecule to the fluorescence of the quencher molecule when the oligonucleotide probe is in a single-stranded state. Influences on the value of $RQ^-$ include, for example, the particular reporter and quencher molecules used, the spacing between the reporter and quencher molecules nucleotide sequence specific effects, and the degree of flexibility of structures, e.g., linkers, to which the reporter and quencher molecules are attached, and the presence of impurities. Wo et al., Anal. Biochem., 218:1–13 (1994); and Clegg, Meth. Enzymol., 211: 353–388 (1992). A related quantity $RQ^+$, refers to the ratio of fluorescent emissions of the reporter molecule to the quencher molecule when the oligonucleotide probe is hybridized to a complementary polynucleotide.

A second factor is the efficiency of the probe to hybridize to a complementary polynucleotide. This second factor depends on the probe's melting temperature, $T_m$, the presence of a secondary structure in the probe or target polynucleotide, the annealing temperature, and other reaction conditions.

A third factor is the efficiency with which the DNA polymerase 5'→3' exonuclease activity cleaves the bound probe between the reporter molecule and quencher molecule. This efficiency depends on such factors as the proximity of the reporter or quencher to the 5' end of the probe, the "bulkiness" of the reporter or quencher, and the degree of complementarity between the probe and target polynucleotide. Lee et al., Nucleic Acids Research, 21: 3761–3766 (1993).

Since quenching depends on the physical proximity of the reporter molecule to the quencher molecule, it was previously assumed that the quencher and reporter molecules must be attached to the probe such that the quencher molecule remains at all times within the maximum distance at which the quencher molecule can quench the reporter molecule, this distance generally being a separation of about 6–16 nucleotides. Lee et al., Nucleic Acids Research, 21: 3761–3766 (1993); Mergny et al., Nucleic Acids Research 22: 920–928 (1994); Cardullo et al., Proc. Natl. Acad. Sci., 85: 8790–8794 (1988); Clegg et al., Proc. Natl. Acad. Sci., 90: 2994–2998 (1993); and Ozaki et al., Nucleic Acids Research, 20: 5205–5214 (1992). This short separation between the reporter molecule and the quencher molecule is typically achieved by attaching one member of the reporter-quencher pair to the 3' or 5' end of the probe and the other member to an internal base 6–16 nucleotides away.

There are at least two significant disadvantages associated with attaching a reporter or quencher molecule to an internal base. Attaching all a reporter or quencher molecule to an internal nucleotide typically involves more difficult chemistry than the chemistry required to attach the molecule to a terminal nucleotide. In addition, attachment of a reporter or quencher molecule to an internal nucleotide can adversely affect the hybridization efficiency of the probe. Ward et al., U.S. Pat. 5,328,824; and Ozaki et al., Nucleic Acids Research, 20: 5205–5214 (1992).

A need currently exists for effective oligonucleotide probes containing a fluorescent reporter molecule and a quencher molecule for use in hybridization and nucleic acid amplification assays. Accordingly, a need exists for probes which exhibit distinguishable fluorescence characteristics when hybridized and not hybridized to a target nucleic acid sequence. A further need exists for probes where the reporter molecule and quencher molecule are positioned on the probe such that the quencher molecule can effectively quench the fluorescence of the reporter molecule. A further need exists for probes which are efficiently synthesized. Yet a further need exists for the reporter molecule and quencher molecule to be positionable on the probe such that the reporter and quencher molecules do not adversely impact the hybridization efficiency of probe. These and further objectives are provided by the probes and methods of the present invention.

SUMMARY OF THE INVENTION

The present invention relates to an oligonucleotide probe which includes a fluorescent reporter molecule and a quencher molecule capable of quenching the fluorescence of the reporter molecule. According to the present invention, the oligonucleotide probe is constructed such that the probe exists in at least one single-stranded confirmation when unhybridized where the quencher molecule is near enough to the reporter molecule to quench the fluorescence of the reporter molecule. The oligonucleotide probe also exists in at least one confirmation when hybridized to a target polynucleotide where the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence until the probe is either hybridized or digested.

According to the present invention, the fluorescence intensity of the reporter molecule is preferably greater than the fluorescence intensity of the quencher molecule when the probe is hybridized to the target polynucleotide. The fluorescence intensity of the reporter molecule is more preferably at least about a factor of 3.5 greater than the fluorescence intensity of the quencher molecule when the probe is hybridized to the target polynucleotide.

The fluorescence intensity of the oligonucleotide probe hybridized to the target polynucleotide is also preferably at least about a factor of 6 greater than the fluorescence intensity of the oligonucleotide probe when not hybridized to the target polynucleotide.

The reporter molecule is preferably separated from the quencher molecule by at least about 15 nucleotides, more preferably at least about 18 nucleotides. The reporter molecule is preferably separated from the quencher molecule by between about 15 and 60 nucleotides, more preferably between about 18 and 30 nucleotides.

The reporter molecule is preferably attached to either the 3' or 5' terminal nucleotides of the probe. The quencher molecule is also preferably attached to either the 3' or 5' terminal nucleotides of the probe. More preferably, the reporter and quencher molecules are attached to the 3' and 5' or 5' and 3' terminal nucleotides of the probe respectively.

The reporter molecule is preferably a fluorescein dye and the quencher molecule is preferably a rhodamine dye.

In one embodiment, the oligonucleotide probe of the present invention is immobilized on a solid support. The oligonucleotide probe may be attached directly to the solid support, for example by attachment of the 3' or 5' terminal nucleotide of the probe to the solid support. More preferably, however, the probe is attached to the solid support by a linker. The linker serves to distance the probe from the solid support. The linker is most preferably at least 30 atoms in length, more preferably at least 50 atoms in length.

A wide variety of linkers are known in the art which may be used to attach the oligonucleotide probe to the solid support. The linker most preferably includes a functionalized polyethylene glycol because it does not significantly interfere with the hybridization of probe to the target oligonucleotide, is commercially available, soluble in both organic and aqueous media, easy to functionalize, and completely stable under oligonucleotide synthesis and post-synthesis conditions.

The linkages between the solid support, the linker and the probe are preferably not cleaved during removal of base protecting groups under basic conditions at high temperature. Examples of preferred linkages include carbamate and amide linkages.

The present invention also relates to the use of the oligonucleotide probe as a hybridization probe to detect target polynucleotides. Accordingly, the present invention relates to a hybridization assay for detecting the presence of a target polynucleobde in a sample. In one embodiment of the method, the hybridization probe is immobilized on a solid support.

According to the method, an oligonucleotide probe of the present invention is contacted with a sample of polynucleofides under conditions favorable for hybridization. The fluorescence signal of the reporter molecule before and after being contacted with the sample is compared. Since the reporter molecule on the probe exhibits a greater fluorescence signal when hybridized to a target sequence, an increase in the fluorescence signal after the probe is contacted with the sample indicates the hybridization of the probe to target sequences in the sample, thereby indicating the pressure of target sequences in the sample. Quantification of the change in fluorescence intensity as a result of the probe being contacted with the sample can be used to quantify the amount of target sequences present in the sample.

The present invention also relates to the use of the oligonucleotide probe for monitoring nucleic acid amplification. Accordingly, the present invention relates to a method for monitoring nucleic acid amplification by performing nucleic acid amplification on a target sequence using a nucleic acid polymerase having 5'→3' nuclease activity, a primer capable of hybridizing to the target sequence and an oligonucleotide probe according to the present invention which is capable of hybridizing to the target sequence 3' relative to the primer. According to the method, the nucleic acid polymerase digests the oligonucleotide probe during amplification when it is hybridized to the target sequence, thereby separating the reporter molecule from the quencher molecule. As the amplification is conducted, the fluorescence of the reporter molecule is monitored, the generation of fluorescence corresponding to the occurrence of nucleic acid amplification. Accordingly, the amount of amplification performed can be quantified based on the change in fluorescence observed. It is noted that the fluorescence of the quencher molecule may also be monitored, either separately or in combination with the reporter molecule, to detect amplification.

BRIEF DESCRIPTION OF THE FIGURES

Figure 1:
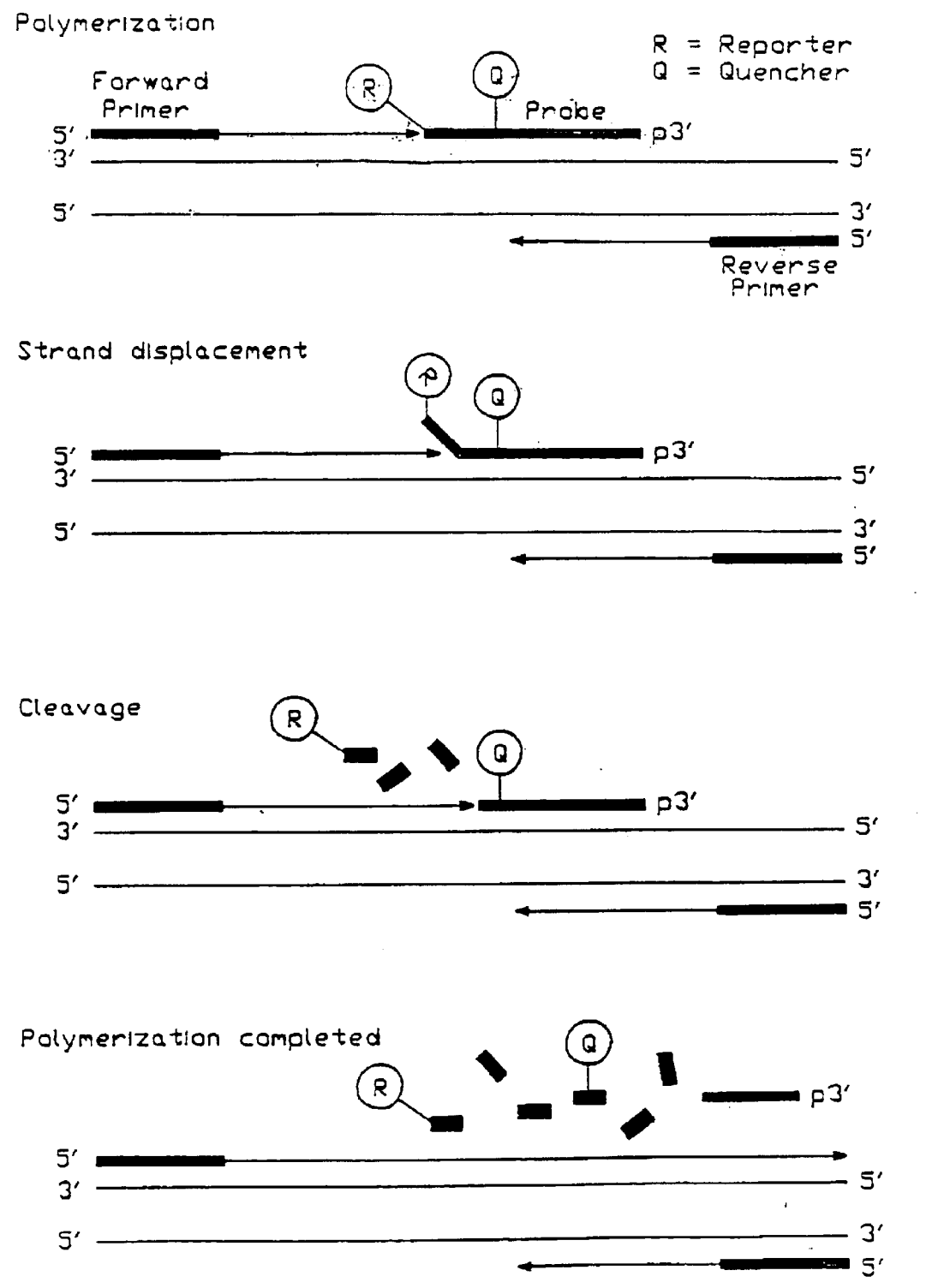

FIG. 1 illustrates a method for real-time monitoring nucleic acid amplification utilizing a probe which is degraded by the 5'→3' exonuclease activity of a nucleic acid polymerase.

DETAILED DESCRIPTION

Figure 2:
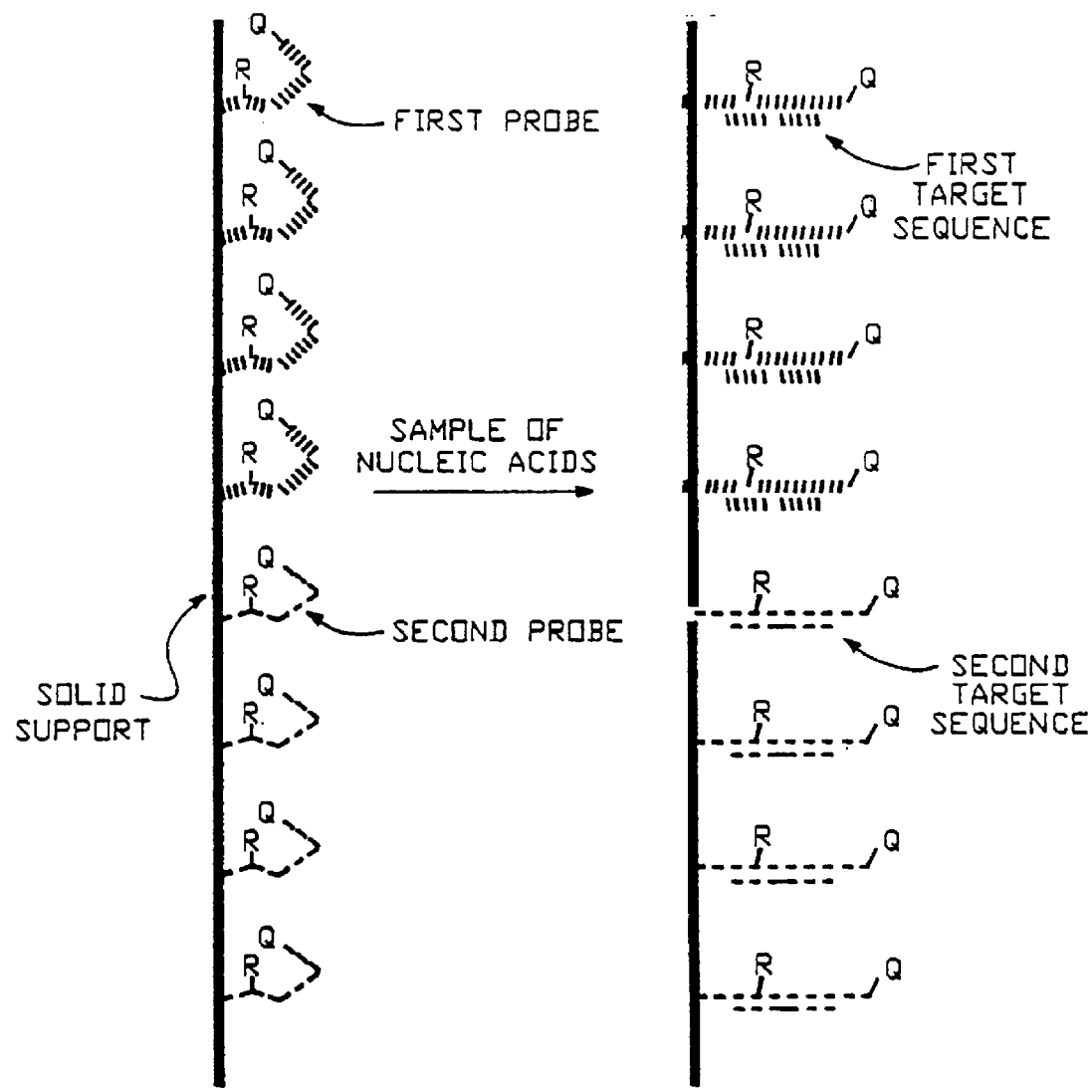
FIG. 2 illustrates a probe according to the present invention immobilized to a solid support in hybridized and unhybridized conformations.

The present invention relates to an oligonucleotide probe which includes a fluorescent reporter molecule and a quencher molecule capable of quenching the fluorescence of the reporter molecule. According to the present invention, the oligonucleotide probe is constructed such that the probe exists in at least one single-stranded confirmation when unhybridized where the quencher molecule is near enough to the reporter molecule to quench the fluorescence of the reporter molecule. The oligonucleotide probe also exists in at least one confirmation when hybridized to a target polynucleotide such that the quencher molecule is not positioned close enough to the reporter molecule to quench the fluorescence of the reporter molecule. By adopting these hybridized and unhybrdized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence unless the probe is either hybridized or digested.

According to the present invention, the fluorescence intensity of the reporter molecule is preferably greater than the fluorescence intensity of the quencher molecule when the probe is hybridized to the target polynucleotide. The fluorescence intensity of the reporter molecule is more preferably at least about a factor of 3.5 greater than the fluorescence intensity of the quencher molecule when the probe is hybridized to the target polynucleotide.

The fluorescence intensity of the oligonucleotide probe hybridized to the target polynucleotide is also preferably at least about a factor of 6 greater than the fluorescence intensity of the oligonucleotide probe when not hybridized to the target polynucleotide.

The reporter molecule is preferably separated from the quencher molecule by at least about 15 nucleotides, more preferably at least about 18 nucleotides. The reporter molecule is preferably separated from the quencher molecule by between about 15 and 60 nucleotides, more preferably between about 18 and 30 nucleotides.

The reporter molecule is preferably attached to either the 3' or 5' terminal nucleotides of the probe. The quencher molecule is also preferably attached to either the 3' or 5' terminal nucleotides of the probe. More preferably, the reporter and quencher molecules are attached to the 3' and 5' or 5' and 3' terminal nucleotides of the probe respectively.

The reporter molecule is preferably a fluorescein dye and the quencher molecule is preferably a rhodamine dye.

In one embodiment, the oligonucleotide probe is attached to a solid support. As illustrated in FIG. 2, when the probe is unhybridized, the probe is able to adopt at least one single-stranded confirmation such that the quencher molecule is near enough to the reporter molecule to quench the fluorescence of the reporter molecule. As further illustrated in FIG. 2, when the probe is hybridized to a target sequence, the probe adopts at least one confirmation where the quencher molecule is not positioned close enough to the reporter molecule to quench the fluorescence of the reporter molecule. As a result, the fluorescence intensity of the reporter molecule increases when the probe hybridizes to a target sequence.

As illustrated in FIG. 2, different probes may be attached to the solid support and may be used to simultaneously detect different target sequences in a sample. Reporter molecules having different fluorescence wavelengths can be used on the different probes, thus enabling hybridization to the different probes to be separately detected.

Examples of preferred types of solid supports for immobilization of the oligonucleotide probe include controlled pore glass, glass plates, polystyrene, avidin coated polystyrene beads cellulose, nylon, acrylamide gel and activated dextran. CPG, glass plates and high cross-linked polystyrene. These solid supports are preferred for hybridization and diagnostic studies because of their chemical stability, ease of functionalization and well defined surface area. Solid supports such as controlled pore glass (CPG, 500 Å, 1000 Å) and non-swelling high cross-linked polystyrene (1000 Å) are particularly preferred in view of their compatibility with oligonucleotide synthesis.

The oligonucleotide probe may be attached to the solid support in a variety of manners. For example, the probe may be attached to the solid support by attachment of the 3' or 5' terminal nucleotide of the probe to the solid support More preferably, however, the probe is attached to the solid support by a linker which serves to distance the probe from the solid support. The linker is most preferably at least 30 atoms in length, more preferably at least 50 atoms in length.

The length and chemical stability of linker between solid support and the first 3' unit of oligonucleotides play an important role in efficient synthesis and hybridization of support bound oligonucleotides. The linker arm should be sufficiently long so that a high yield (>97%) can be achieved during automated synthesis. The required length of the linker will depend on the particular solid support used. For example, a six atom linker is generally sufficient to achieve a >97% yield during automated synthesis of oligonucleotides when high cross-linked polystyrene is used as the solid support. The linker arm is preferably at least 20 atoms long in order to attain a high yield (>97%) during automated synthesis when CPG is used as the solid support.

Hybridization of a probe immobilized to a solid support generally requires that the probe be separated from the solid support by at least 30 atoms, more-preferably at least 50 atoms. In order to achieve this separation, the linker generally includes a spacer positioned between the linker and the 3' nucleoside. For oligonucleotide synthesis, the linker arm is usually attached to the 3'—OH of the 3' nucleoside by an ester linkage which can be cleaved with basic reagents to free the oligonucleotide from the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. Such polymers are preferred over homopolymeric oligonucleotides because they do not significantly interfere with the hybridization of the probe to the target oligonucleotide. Polyethylene glycol is particularly preferred because it is commercially available, soluble in both organic and aqueous media, easy to functionalize, and completely stable under oligonucleotide synthesis and post-synthesis conditions.

The linkages between the solid support, the linker and the probe are preferably not cleaved during removal of base protecting groups under basic conditions at high temperature. Examples of preferred linkages include carbamate and amide linkages.

The oligonucleotide probe of the present invention may be used as a hybridization probe to detect target polynucleotides. Accordingly, the present invention relates to a hybridization assay for detecting the presence of a target polynucleotide in a sample. According to the method, an oligonucleotide probe of the present invention is contacted with a sample of nucleic acids under conditions favorable for hybridization. The fluorescence signal of the reporter molecule is measured before and after being contacted with the sample. Since the reporter molecule on the probe exhibits a greater fluorescence signal when hybridized to a target sequence, an increase in the fluorescence signal after the probe is contacted with the sample indicates the hybridization of the probe to target sequences in the sample and hence the presence of target sequences in the sample. Further, by quantifying the change in fluorescence intensity as a result of the probe being contacted with the sample, the amount of target sequences in the sample can be quantified.

According to one embodiment of the method, the hybridization probe is immobilized on a solid support. The oligonucleotide probe is contacted with a sample of nucleic acids under conditions favorable for hybridization. The fluorescence signal of the reporter molecule is measured before and after being contacted with the sample. Since the reporter molecule on the probe exhibits a greater fluorescence signal when hybridized to a target sequence, an increase in the fluorescence signal after the probe is contacted with the sample indicates the hybridization of the probe to target sequences in the sample. Immobilization of the hybridization probe to the solid support enables the target sequence hybridized to the probe to be readily isolated from the sample. In later steps, the isolated target sequence may be separated from the solid support and processed (e.g., purified, amplified) according to methods well known in the art depending on the particular needs of the researcher.

The oligonucleotide probe of the present invention may also be used as a probe for monitoring nucleic acid amplification. Accordingly, the present invention relates to a method for monitoring nucleic acid amplification using an oligonucleotide probe according to the present invention which is capable of hybridizing to the target sequence 3' relative to an amplification primer. According to the method, nucleic acid amplification is performed on a target polynucleotide using a nucleic acid polymerase having 5→3' nuclease activity, a primer capable of hybridizing to the target polynucleotide, and an oligonucleotide probe according to the present invention capable of hybridizing to the target polynucleotide 3' relative to the primer. During amplification, the nucleic acid polymerase digests the oligonucleotide probe when it is hybridized to the target sequence, thereby separating the reporter molecule from the quencher molecule. As the amplification is conducted, the fluorescence of the reporter molecule is monitored, the generation of fluorescence corresponding to the occurrence of nucleic acid amplification.

Use of a reporter-quencher pair probe generally in conjunction with the amplification of a target polynucleotide, for example, by PCR, e.g., is described in many references, such as Innis et al., editors, PCR Protocols (Academic Press, New York, 1989); Sambrook et al., Molecular Cloning, Second Edition (Cold Spring Harbor Laboratory, New York, 1989), each of which are incorporated herein by reference. The binding site of the oligonucleotide probe is located between the PCR primers used to amplify the target polynucleotide. Preferably, PCR is carried out using Taq DNA polymerase, e.g., Amplitaq™ (Perkin-Elmer, Norwalk, Conn.), or an equivalent thermostable DNA polymerase, and the annealing temperature of the PCR is about 5–10° C. below the melting temperature of the oligonucleotide probes employed.

Use of an oligonucleotide probe according to the present invention for monitoring nucleic acid amplification provides several advantages over the use of prior art reporter-quencher pair probes. For example, prior art probes required that the reporter and quencher molecules be positioned on the probe such that the quencher molecule remained within a minimum quenching distance of the reporter molecule. However, by realizing that the probe need only be designed such that the probe be able to adopt a confirmation where the quencher molecule is within a minimum quenching distance of the reporter molecule, a far wider array of probes are enabled. For example, dually labelled probes having the reporter and quencher molecules at the 5' and 3' ends can be designed. Such probes are far easier to synthesize than probes where the reporter molecule or the quencher molecule is attached to an internal nucleotide. Positioning of the reporter and quencher molecules on terminal nucleotides also enhances the hybridization efficiency of the probes.

As used in this application, the term "oligonucleotide", includes linear oligomers of natural or modified monomers or linkages, including deoxyribonucleosides, ribonucleosides, and the like; capable of specifically binding a target polynucleotide by way of a regular pattern of monomer-to-monomer interactions, such as Watson-Crick type of basepairing, or the like. Usually monomers are linked by phosphodiester bonds or analogs thereof to form oligonucleotides ranging in size from a few monomeric units, e.g., 3–4, to several tens of monomeric units. Whenever an oligonucleotide is represented by a sequence of letters, such as "ATGCCTG", it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. Generally, oligonucleotide probes of the invention will have a sufficient number of phosphodiester linkages adjacent to its 5' end so that the 5'→3' exonuclease activity employed can efficiently degrade the bound probe to separate the reporter and quencher molecules.

"Perfectly matched" in reference to a duplex means that the poly- or oligonucleotide strands making up the duplex form a double-stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. Conversely, a "mismatch" in a duplex between a target polynucleotide and an oligonucleotide probe or primer means that a pair of nucleotides in the duplex fails to undergo Watson-Crick bonding.

As used in the application, "nucleoside" includes the natural nucleosides, including 2'-deoxy and 2'-hydroxyl forms, e.g., as described in Komberg and Baker, DNA Replication, 2nd Ed. (Freeman, San Francisco, 1992). "Analogs" in reference to nucleosides includes synthetic nucleosides having modified base moieties and/or modified sugar moieties, e.g., described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce degeneracy, increase specificity, and the like. Oligonucleotide probes of the invention can be synthesized by a number of approaches, e.g., Ozaki et al., Nucleic Acids Research, 20: 5205–5214 (1992); Agrawal et al., Nucleic Acids Research, 18: 5419–5423 (1990); or the like. The oligonucleotide probes of the invention are conveniently synthesized on an automated DNA synthesizer, e.g., an Applied Biosystems, Inc. (Foster City, Calif.) model 392 or 394 DNA/RNA Synthesizer, using standard chemistries, such as phosphoramidite chemistry, e.g., disclosed in the following references: Beaucage and Iyer, Tetrahedron, 48: 2223–2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679; and the like. Alternative chemistries, e.g., resulting in non-natural backbone groups, such as phosphorothioate, phosphoramidate, and the like, may also be employed provided that the hybridization efficiencies of the resulting oligonucleotides and/or cleavage efficiency of the exonuclease employed are not adversely affected.

Preferably, the oligonucleotide probe is in the range of 15–60 nucleotides in length. More preferably, the oligonucleotide probe is in the range of 18–30 nucleotides in length. The precise sequence and length of an oligonucleotide probe of the invention depends in part on the nature of the target polynucleotide to which it binds. The binding location and length may be varied to achieve appropriate annealing and melting properties for a particular embodiment. Guidance for making such design choices can be found in many of the above-cited references describing the "Taq-man" type of assays.

Preferably, the 3' terminal nucleotide of the oligonucleotide probe is blocked or rendered incapable of extension by a nucleic acid polymerase. Such blocking is conveniently carried out by the attachment of a reporter or quencher molecule to the terminal 3' carbon of the oligonucleotide probe by a linking moiety.

Preferably, reporter molecules are fluorescent organic dyes derivatized for attachment to the terminal 3' carbon or terminal 5' carbon of the probe via a linking moiety. Preferably, quencher molecules are also organic dyes, which may or may not be fluorescent, depending on the embodiment of the invention. For example, in a preferred embodiment of the invention, the quencher molecule is fluorescent. Generally whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to in the application as chromogenic molecules.

There is a great deal of practical guidance available in the literature for selecting appropriate reporter-quencher pairs for particular probes, as exemplified by the following references: Clegg (cited above); Wu et al., (cited above); Pesce et al., editors, Fluorescence Spectroscopy (Marcel Dekker, New York, 1971); White et al., Fluorescence Analysis: A Practical Approach (Marcel Dekker, New York, 1970); and the like. The literature also includes references providing exhaustive lists of fluorescent and chromogenic molecules and their relevant optical properties for choosing reporter-quencher pairs, e.g., Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland (cited above); Ullman et al., U.S. Pat. No. 3,996,345; Khanna et al., U.S. Pat. No. 4,351,760; and the like.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Preferably, reporter and quencher molecules are selected from fluorescein and rhodamine dyes. These dyes and appropriate linking methodologies for attachment to oligonucleotides are described in many references, e.g., Khanna et al., (cited above); Marshall, Histochemical J., 7: 299–303 (1975); Menchen et al., U.S. Pat. No. 5,188,934; Menchen et al., European Patent Application 87310256.0; and Bergot et al., International Application PCT/US90/05565. The latter four documents are hereby incorporated by reference.

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305–5321 (1987) (3' thiol group on oligonucleotide); Sharma et al., Nucleic Acids Research, 19: 3019 (1991) (3' sulfhydryl); Giusti et al., PCR Methods and Applications, 2: 223–227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); Agrawal et al., Tetrahedron Letters, 31: 1543–1546 (1990) (attachment via phosphoramidate linkages); Sproat et al., Nucleic Acids Research, 15: 4837 (1987) (5' mercapto group); Nelson et al., Nucleic Acids Research, 17: 7187–7194 (1989) (3' amino group); and the like.

Preferably, commercially available linking moieties are employed that can be attached to an oligonucleotide during synthesis, e.g., available from Clontech Laboratories (Palo Alto, Calif.).

Rhodamine and fluorescein dyes are also conveniently attached to the 5' hydroxyl of an oligonucleotide at the conclusion of solid phase synthesis by way of dyes derivatized with a phosphoramidite moiety, e.g., Woo et al., U.S. Pat. No. 5,231,191; and Hobbs, Jr., U.S. Pat. No. 4,997,928.

The following examples set forth probes and methods for using the probes according to the present invention. It is understood that the specific probes, probe constructs and steps of the methods described in these examples are not intended to be limiting. Further objectives and advantages of the present invention other than those set forth above will become apparent from the examples which are not intended to limit the scope of the present invention.

EXAMPLES

1. Synthesis of Oligonucleotide Probes

The following example describes the synthesis of the oligonucleotides shown in Table 1. Linker arm nucleotide ("LAN") phosphoramidite was obtained from Glen Research. Standard DNA phosphoramidites, 6-carboxyfluorescein ("6FAM") phosphoramidite, 6-carboxytetramethylrhodamine succinimidyl ester ("TAMRA NHS ester"), and Phosphalink™ for attaching a 3' blocking phosphate were obtained from Perkin-Elmer, Applied Biosystems Division. Oligonucleotide synthesis was performed on a model 394 DNA Synthesizer (Applied Biosystems). Primer and complement oligonucleotides were purified using Oligo Purification Cartridges (Applied Biosystems). Doubly labeled probes were synthesized with 6-FAM-labeled phosphoramidite at the 5' end, LAN replacing one of the T's in the oligonucleotide sequence, and Phosphalink™ at the 3' end. Following deprotection and ethanol precipitation, TAMRA NHS ester was coupled to the LAN-containing oligonucleotide in 250 mM Na-bicarbonate buffer (pH 9.0) at room temperature. Unreacted dye was removed by passage over a PD-10 Sephadex column. Finally, the doubly labeled probe was purified by preparative HPLC using standard protocols. Below, probes are named by designating the sequence from Table 1 and the position of the LAN-TAMRA moiety. For example, probe A1-7 has sequence of A1 with LAN-TAMRA at nucleoside position 7 from the 5' end.

TABLE 1

Sequences of oligonucleotides

| Name | Type | Sequence |
| --- | --- | --- |
| F119 | primer | ACCCACAGGAACTGATCACCACTC [SEQ. ID. No.: 1] |
| R119 | primer | ATGTCGCGTTCCGGCTGACGTTCTGC [SEQ. ID. No.: 2] |
| P2 | probe | TCGCATTACTGATCGTTGCCAACCAGTp [SEQ. ID. No.: 3] |
| P2C | complement | GTACTGGTTGGCAACGATCAGTAATGCGATG [SEQ. ID. No.: 4] |
| P5 | probe | CGGATTTGCTGGTATCTATGACAAGGATp [SEQ. ID. No.: 5] |
| P5C | complement | TTCATCCTTGTCATAGATACCAGCAAATCCG [SEQ. ID. No.: 6] |
| AFP | primer | TCACCCACACTGTGCCCATCTACGA [SEQ. ID. No.: 7] |
| ARP | primer | CAGCGGAACCGCTCATTGCCAATGG [SEQ. ID. No.: 8] |
| A1 | probe | ATGCCCTCCCCCATGCCATCCTGCGTp [SEQ. ID. No.: 9] |
| A1C | complement | AGACGCAGGATGGCATGGGGGAGGGCATAC [SEQ. ID. No.: 10] |
| A3 | probe | CGCCCTGGACTTCGAGCAAGAGATp [SEQ. ID. No.: 11] |
| A3C | complement | CCATCTCTTGCTCGAAGTCCAGGGCGAC [SEQ. ID. No.: 12] |
| G1 | probe | CAAGCTTCCCGTTCTCAGCCT [SEQ. ID. No.: 13] |
| G1C | complement | ACCGTCAAGGCTGAGAACGGGAAGCTTGTC [SEQ. ID. No.: 14] |

TABLE 2

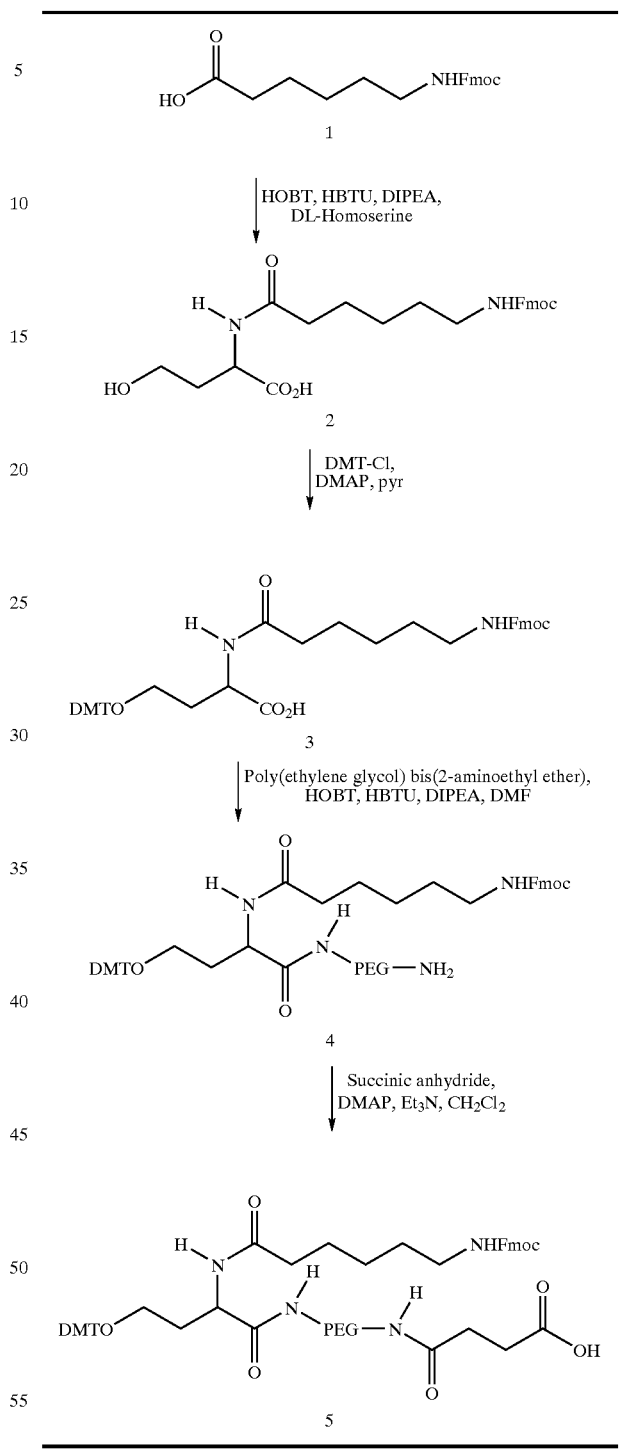

TABLE 3

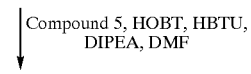

TABLE 3-continued

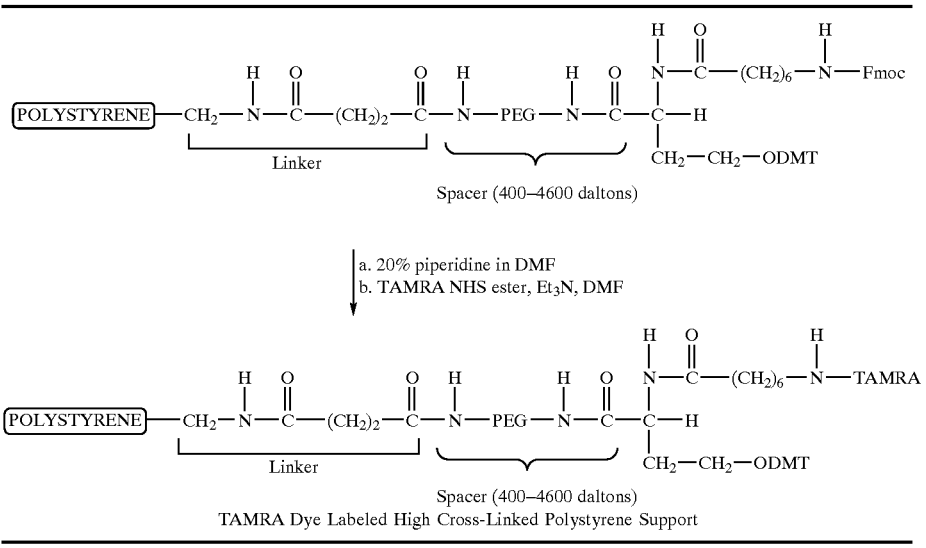

TAMRA Dye Labeled High Cross-Linked Polystyrene Support

TABLE 4

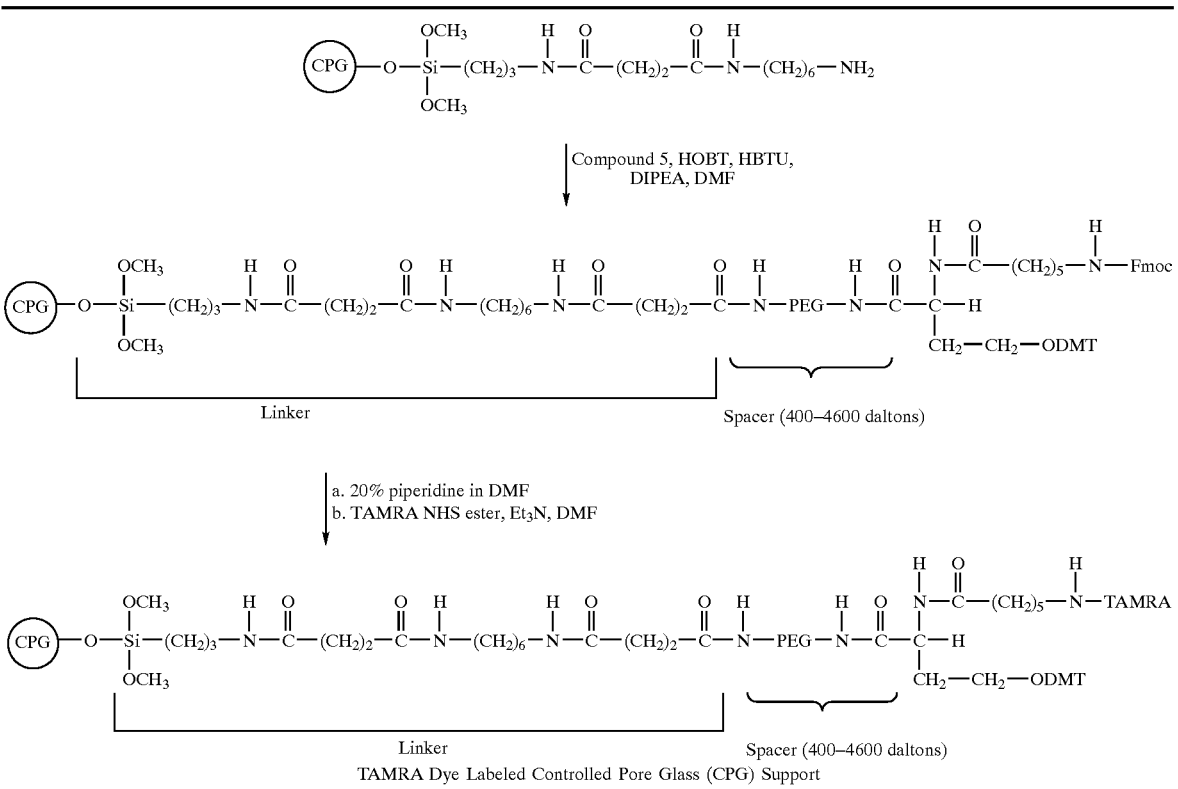

TAMRA Dye Labeled Controlled Pore Glass (CPG) Support

2. Synthesis of Oligonucleotide Probes Attached To A Solid Support

Both high cross-linked polystyrene (1000 Å) and controlled pore glass (CPG) (500 Å) are used as solid support matrices. The functionalization of a spacer (compound 5) is illustrated in Table 2. The attachment of the spacer to polystyrene and CPG supports, and the labelling of the solid supports with TAMRA dye is shown in Tables 3 and 4 respectively.

Table 2 illustrates a reaction scheme for the synthesis of a spacer, compound 5, which is used to derivative CPG and polystyrene supports. As shown in Table 2, N-Fmoc-ε-aminocaproic acid was reacted with DL-homoserine in presence of HOBT/HBTU/DIPEA (Knorr, et al., *Tetrahedron Lett*. 1989, 30, 1927) in DMF to give compound 2 in 65% yield. Compound 2 was reacted with dimethoxytrityl chloride in presence of DMAP in pyridine to give compound 3 in 72% yield after chromatography. Treatment of compound 3 with a large excess of PEG-diamine (Buckmann, et al., *Biotech. Appl. Biochem.* 1987, 9, 258) in presence of HOBT/HBTU/DIPEA in DMF afforded amine 4 in 60% yield. The amine 4 was then converted to succinate 5 by treating amine 4 with succinic anhydride/Et$_3$N/DMAP in CH$_2$Cl$_2$ in 90% yield. The succinate 5 was then attached to polystyrene and CPG support as illustrated in Tables 3 and 4 respectively without further purification.

As illustrated in Tables 3 and 4, succinate 5 was separately reacted with polystyrene and CPG support in presence of HOBT/HBTU/DIPEA in DMF to provide functionalized support 6 (5 μmol/g loading) and functionalized support 8 (15 μmol/g loading) respectively. The Fmoc group was removed from support bound spacer by treating supports 6 and 8 with 20% piperidine in DMF (Fields, et al., *J. Peptide Res.* 1990, 35, 161) to give amine which was reacted with TAMRA NHS ester to give TAMRA labeled supports 7 and 9 respectively. The polystyrene and CPG supports showed a final loading of 4.8 μmol/g and 14 μmol/g respectively by trityl cation assay.

Double labeled Taqman probe was synthesized using both TAMRA labeled supports 7 and 9, FastPhoramidites (User Bulletin Number 85, Perkin Elmer Corporation 1994) and FAM phosphoramidite (User Bulletin Number 78, Perkin Elmer Corporation 1994) in 40 nanomol scale. The support bound oligonucleotides were deprotected by treating with MeOH:t-BuNH$_2$:H$_2$O (1:1:2) at 65° C. for 3 hours (Woo, et al., U.S. Pat. No. 5,231,191). Liquid was removed and the support containing probes were washed with H$_2$O:MeOH (3:1) and MeOH. The support was then dried under vacuum and used in a hybridization assay.

Experimental:

Compound 2: N,N-Diisopropylethylamine (1.1 g, 1.48 mL, 8.52 mmol), 1-hydroxybenzotriazol (420 mg, 3.1 mmol) and (2-(1H-benzotriazol-1-yl)-1,1,3,3-tetramethyluronium hexafluorophosphate (1.17 g, 3.1 mmol) were added to a stirred solution of Nfmoc-ε-aminocaproic acid (1 g, 2.84 mmol) in DMF (30 mL) at room temperature. After 15 min DL-homoserine (1.35 g, 11.36 mmol) was added to the reaction mixture. After 3 hours, DMF was removed under reduced pressure. The residue was dissolved in CHCl$_3$ (100 mL) and washed with 5% aqueous HCl (2×50 mL). The organic layer was dried over MgSO$_4$ and evaporated to give a thick oil which was trituated with ether to give a colorless solid (840 mg, 65%). The product was left under high vacuum for 24 hours and used in the next step without further purification.

Compound 3: 4,4'-Dimethoxytrityi chloride (484 mg, 1.43 mmol) and 4-dimethyaminopyridine (25 mg, 0.2 mmol) were added to a stirred solution of compound 2 (500 mg, 1.1 mmol) in pyridine (15 mL) at room temperature under nitrogen atmosphere. After 14 hours, pyridine was removed and the residue was dissolved in CHCl$_3$ (70 mL). The organic layer was extracted with 5% aqueous citric acid (1×50 mL), H$_2$O (1×50 mL) and saturated brine (1×50 mL). The organic layer was dried over MGSO$_4$ and evaporated to give a yellow foam. The product was purified by a silica gel column eluting with CHCl$_3$-MeOH gradient (0–10% MeOH). The appropriate fractions were combined and evaporated to give Compound 3 as a colorless foam (600 mg, 72%).

Compound 4: Poly(ethylene glycol) bis(2-aminoethyl ether) (3.16 g, 5.3 mmol), N,N-diisopropylethylamine (205 mg, 0.27 mL, 1.59 mmol), 1-hydroxybenzotriazol (78 mg, 0.58 mmol) and (2-(1H-benzotriazol-1-yl)-1,1,3,3-tetramethyluonium hexafluorophosphate (220 mg, 0.58 mmol) were added to a stirred solution of compound 3 (400 mg, 0.53 mmol) in DMF (10 mL) at room temperature. The reaction mixture was stirred at room temperature for 3 hours. DMF was removed under reduced pressure and, the residue was dissolved in CHCl$_3$ (70 mL) and washed with H$_2$O (1×50 mL) and saturated brine (2×50 mL). The organic layer was dried over MgSO$_4$ and evaporated to give a thick oil. Compound 4 was purified by a silica gel column eluting with a CHCl$_3$-MeOH gradient (5–15% MeOH) as a colorless glass (423 mg, 60%).

Compound 5: Succinic anhydride (22 mg, 0.22 mmol), Et$_3$N (23 mg, 0.31 μL, 0.22 mmol), 4-dimethylaminopyridine (14 mg, 0.11 mmol) were added to a solution of compound 4 (300 mg, 0.22 mmol) in CH$_2$Cl$_2$ (15 mL). The reaction mixture was stirred at room temperature for 3 hours. The reaction mixture was diluted with CHCl$_3$ (30 mL) and washed with 5% aqueous citric acid (1×50 mL) and saturated brine (2×50 mL). The organic layer was dried over MgSO$_4$ and evaporated to a colorless foam (284 mg, 90%) which was used for derivatization of the solid support without further purification.

Derivatization of Polystyrene support with TAMRA dye: High cross linked polystyrene (1000 Å, 10 μmol/g amine loading, 1 g, 10 μmol), was treated with compound 5 (17 mg, 12 μmol, 1-hydroxybenzotriazol (1.8 mg, 12 μmol), (2-(1H-benzotriazol-1-yl)-1,1,3,3-tetramethyluonium hexafluorophosphate (4.8 mg, 12 μmol), N,N-diisopropylethylamine (6 μL, 30 μmol) in DMF (10 mL) on a wrist action shaker for 4 hours at room temperature. The support was washed with DMF (3×10 mL), CH$_3$CN (2×10 mL) and CH$_2$Cl$_2$ (1×10 mL) and dried under high vacuum overnight. The ninhydrin assay showed 1 μmol0g amine left. The trityl cation assay gave 5 μmol/g loading of compound 5. The support was capped with acetic anhydridellutidine in THF (10% solution, 5 mL) and 1-methylimidazol in THF (16% solution, 5 mL) for 2 hours at room temperature. The support was washed with CH$_3$CN (3×10 mL) and CH$_2$Cl$_2$ (1×10 mL). The support was treated with 20% piperidine in DMF (3×10 mL) to remove the Fmoc protecting group. The removal of the Fmoc group was monitored by measuring UV of the solution at 302 nm. The support was washed with DMF (3×10 mL) and, then treated with TAMRA NHS ester (15 mg, 27 μmol) and Et$_3$N (50 μmol) in DMF (10 mL) for 42 hours on a shaker. The support was washed with DMF (3×10 mL) CH$_3$CN (2×10 mL) and CH$_2$Cl$_2$ (1×10 mL) and dried under high vacuum for 24 hours. Ninhydrin test showed less than 0.5 μmol/g amine left. The support was capped with acetic anhydride/lutidine in THF (10% solution, 5 mL) and 1-methylimidazol in THF (16% solution, 5 mL) for 1 hour and then washed with CH$_3$CN (3×10 mL), CH$_2$Cl$_2$ (2×10 mL) and dried under high vacuum for 24 hour. The trityl cation assay showed a final loading of 4.8 μmol/g.

Derivatization of CPG support with TAMRA dye: A mixture of CPG (500 Å, 40 μmol/g amine loading, 500 mg, 20 μmol), compound 5 (31 mg, 22 μmol), 1-hydroxybenzotriazol (5.9 mg, 22 μmol), (2-(1H-benzotriazol-1-yl)-1,1,3,3-tetramethyluronium hexafluorophosphate (8.4 mg, 22 μmol), N,N-diisopropylethylamine (10.4 μL, 60 μmol) in DMF (10 mL) was shaken on a wrist action shaker for 4 hours at room temperature. The support was washed with DMF (3×10 mL), CH$_3$CN (2×10 mL) and CH$_2$Cl$_2$ (1×10 mL) and dried under high vacuum overnight. The ninhydrin assay showed 4 μmol/g amine left. The trityl assay gave 15 μmol/g loading of compound 5 on CPG support. The support was capped with acetic anhydridenlu-tidine in THF (10% solution, 5 mL) and 1-methylimidazol in THF (16% solution, 5 mL) for 2 hours at room temperature. The support was washed with CH$_3$CN (3×10 mL) and CH₂Cl₂ (1×10 mL). The support was treated with 20% piperidine in DMF (3×10 mL) to remove the Fmoc protecting group. Removal of the Fmoc group was monitored by measuring UV of the solution at 302 nm. The support was washed with DMF (3×10 mL). The support was then treated with TAMRA NHS ester (25 mg, 45 μmol) and Et₃N (90 μmol) in DMF (5 mL) for 42 hours on a shaker. The support was washed with DMF (3×10 mL), CH₃CN (2×10 mL) and CH₂Cl₂ (1×10 mL) and dried under high vacuum for 24 hours. Ninhydrin test showed less than 1 μmol/g amine left. The support was capped with acetic anhydride/lutidine in THF (10% solution, 5 mL) and 1-methylimidazol in THF (16% solution, 5 mL) for 1 hour and then washed with CH₃CN (3×10 mL), CH₂Cl₂ (2×10 mL) and dried under high vacuum for 24 hours. The trityl cation assay showed a final loading of 14 μmol/g.

Synthesis of FAM and TAMRA Doubled Labeled Probes: Doubled dye labeled oligonucleotide probe were synthesized by using TAMRA labelled supports 7 and 9, DNA FastPhosphoramidite and FAM amidite in 40 nmol scale. After completion of synthesis, supports containing probes were transferred to 4 mL glass vials and treated with a mixture of MeOH:t-BuNH₂:H₂O (1:1:2) at 65 °C. for 3 hours. Liquid was removed by a syringe and the support was washed with H₂O:MeOH (3:1) and MeOH. The support was dried under vacuum and used in the hybridization assay.

3. Hybridization Assay Using Oligonucleotide Probe

A 295 basepair segment of exon 3 of human beta-actin gene (nucleotides 2141–2435 as disclosed in Nakajima-lijima, S., *Proc. Natl. Acad. Sci. USA* 82: 6133–6137 (1985) can be amplified using 50 ul reactions that contain 10 mM Tris-HCl (pH 8.3), 50 mM KCl, 4 mM MgCl₂, 300 nM primer AFP [SEQ. I.D. No. 7], 300 nM primer biotin-ARP [SEQ. I.D. No. 8 with biotin attached to the 5' end], 200 μM dATP, 200 μM dCTP, 200 μM dGTP, 200 μM TTP, and 1.25 units AmpliTaq (Perkin-Elmer). The reactions are performed with (+template) or without (no template) 20 ng human genomic DNA.

After thermal cycling at 50° C. (2 min); 95° C. (10 min); and 40 cycles of 95° C. (20 sec) followed by 60° C. (1 min), each sample is diluted by adding 200 μl Hybridization Buffer (5×SSC, 8% (v/v) formamide, 8% (v/v) Triton X-100). The resulting samples are transferred to a streptavidin-coated 96-well microtiter plate (Xenopore Corp., Saddle Brook, N.J.) and incubated at 37° C. for 30 min in order to capture the amplified beta-actin DNA segment. Each well is then washed with 350 μl phosphate buffered saline/0.05% TWEEN-20. Any unbiotinylated DNA strands are removed by adding 100 μl 0.1 M NaOH/1.mM EDTA, incubating at room temperature for 5 min, and washing with 350 ul phosphate buffered saline/0.05% TWEEN-20. 50 ul of Hybridization Buffer containing 100 nM of probe A1-26 [SEQ. I.D. No. 9, nucleotides 1–26 (A1-26), labeled with reporter FAM and quencher TAMRA) is then added and incubate at 37° C. for 30 min.

Fluorescence is then measured at 518 nm and 582 nm using a Perkin-Elmer TaqMan LS50B System. The ΔRQ is then calculated as described in Example 5. The magnitude of ΔRQ indicates the level of hybridization of the A1-26 probe and thus is a measure of the amount of amplified beta-actin DNA segment captured in each well.

4. Hybridization Assay Using Oligonucleotide Probe Attached To Solid Support Three probe/solid support combinations were examined: A1-PS: A1 [SEQ. I.D. No. 9] attached to polystyrene support; A1-CPG: A1 [SEQ. I.D. No. 9] attached to glass support; and G1-PS: G1 [SEQ. I.D. No. 13] attached to polystyrene support.

All three probes have FAM attached to the 5' end of the sequence and TAMRA attached to the 3' end. No template reactions were prepared by suspending each probe/solid support sample in 50 μl 1×PCR Buffer(10 mM Tris-HCl (pH 8.3), 50 mM KCl, 3.5 mM MgCl₂). For plus template reactions, A1-PS and A1-CPG were suspended in 50 μl 1×PCR Buffer+1 μM A1C; G1-PS was suspended in 50 μl 1×PCR Buffer+1 μM G1C.

Reactions were incubated at 95° C. for 1 min, then allowed to cool slowly to room temperature. A portion of each suspension was placed on a microscope slide. Each sample was excited with 488 nm light and a fluorescence image was captured on a CCD array using either a 518 nm or 583 nm interference filter. The images were analyzed by finding a peak pixel value on the 518 nm image and then finding the 583 nm value for the same pixel. Pixel values were corrected by subtracting the background readings observed with buffer. Table 5 gives the results of fluorescence measurements of the indicated probes.

TABLE 5

| PROBE | 518 | | 582 | | RQ− | RQ+ | ΔRQ |
|---|---|---|---|---|---|---|---|
| | no temp. | +temp. | no temp. | +temp. | | | |
| A1-PS | 149 | 354 | 253 | 379 | 0.42 | 0.67 | 0.25 |
| A1-CPG | 494 | 437 | 1500 | 616 | 1.13 | 2.44 | 1.31 |
| G1-PS | 75 | 166 | 178 | 245 | 0.45 | 0.73 | 0.28 |

5. Method For Monitoring PCR Amplification Using Oligonucleotide Probe

All PCR amplifications were performed in a Perkin-Elmer Thermocycler 9600 using 50 μl reactions that contained 10 mM Tris-HCl (pH 8.3), 50 mM KCl, 200 μM dATP, 200 μM dCTP, 200 μM dGTP, 400 μM dUTP, 0.5 units AmpErase™ uracil N-glycolyase (Perkin-Elmer), and, 1.25 units Ampli-Taq™ (Perkin-Elmer). A 295 basepair segment of exon 3 of human β-actin gene (nucleotides 2141–2435 disclosed by Nakajima-lijima, S., *Proc. Natl. Acad, Sci. USA* 82: 6133–6137 (1985) was amplified using the AFP and ARP primers listed below. The amplification reactions contained 4 mM MgCl₂, 20 ng human genomic DNA, 50 nM A1 or A3 probe, and 300 nM of each primer. Thermal regimen was 50° C. (2 min); 95° C. (10 min); 40 cycles of 95° C. (20 sec); 60 ° C. (1 min); and hold at 72 DC. A 515 basepair segment was amplified from a plasmid that consists of a segment of λ DNA (nucleotides 32, 220–32, 747) inserted into the Sma I site of vector pUC119. These reactions contained 3.5 mM MgCl₂, 1 ng plasmid DNA, 50 nMP2 or P5 probe, 200 nM primer F119, and 200 nM primer R119. The thermal regimen was 50° C. (2 min); 95° C. (10 min); 25 cycles of 95° C. (20 sec), 57° C. (1 min); and hold at 72° C.

For each amplification reaction, 40 μl was transferred to an individual well of a white 96-well microtiter plate (Perkin-Elmer). Fluorescence was measured on a Perkin-Elmer TaqMan™ LS-50B System, which consists of a luminescence spectrometer with a plate reader assembly, a 485 nm excitation filter, and a 515 nm emission filter. Excitation was carried out at 488 nm using a 5 nm slit width. Emission was measured at 518 nm for 6-FAM (the reporter, or R Valve) and 582 nm for TAMRA (the quencher, or Q value) using a 10 nm slit width. In order to determine the increase in reporter emission that is due to cleavage of the probe during PCR, three normalizations are applied to the raw emission data. First, emission intensity of a buffer blank is subtracted for each wavelength. Second, emission intensity of the reporter is divided by the emission intensity of the quencher to give an RQ ratio for each reaction tube. This normalizes for well-to-well variation in probe concentration and fluorescence measurement. Finally, ΔRQ is calculated by subtracting the RQ value of the no template control (RQ⁻) from the RQ value for the complete reaction including a template (RQ⁺).

Three pairs of probes were tested in PCR assays. For each pair, one probe has TAMRA attached to an internal nucleotide and the other has TAMRA- attached to the 3' end nucleotide. Results are shown in Table 6. For all three sets, the probe with the 3' quencher exhibits a ΔRQ value that is considerable higher than for the probe with the internal quencher.

TABLE 6

| PROBE | 518 no temp. | 518 +temp. | 582 no temp. | 582 +temp. | RQ− | RQ+ | ΔRQ |
|---|---|---|---|---|---|---|---|
| A3-6 | 34.06 | 50.1 | 73.78 | 70.8 | 0.5 | 0.71 | 0.25 |
| A3-24 | 58.85 | 202 | 69.66 | 78.8 | 0.8 | 2.57 | 1.72 |
| P2-7 | 67.58 | 341 | 85.78 | 87.9 | 0.8 | 3.89 | 3.1 |
| P2-27 | 124.6 | 722 | 152.6 | 118 | 0.8 | 6.1 | 5.28 |
| P5-10 | 77.32 | 156 | 75.41 | 67 | 1 | 2.33 | 1.3 |
| P5-28 | 73.23 | 507 | 106.6 | 96.3 | 0.7 | 5.28 | 4.59 |

TABLE 7

Fluorescence In Single And Double-stranded States.

| Probe | 518 ss | 518 ds | 582 ss | 582 ds | RQ ss | RQ ds |
|---|---|---|---|---|---|---|
| P2-7 | 63.81 | 84.07 | 96.52 | 142.97 | 0.66 | 0.59 |
| P2-27 | 92.31 | 557.53 | 165.13 | 89.47 | 0.56 | 6.23 |
| P5-10 | 266.30 | 366.37 | 437.97 | 491.00 | 0.61 | 0.75 |
| P5-28 | 51.91 | 782.80 | 141.20 | 154.07 | 0.37 | 5.08 |
| A1-7 | 18.40 | 60.45 | 105.53 | 218.83 | 0.17 | 0.28 |
| A1-26 | 87.75 | 734.37 | 90.91 | 118.57 | 0.97 | 6.19 |
| A3-6 | 44.77 | 104.80 | 90.80 | 177.87 | 0.49 | 0.59 |
| A3-24 | 45.57 | 857.57 | 100.15 | 191.43 | 0.46 | 3.47 |

Table 7 gives the results of fluorescence measurements of the indicated probes in single and double-stranded states. For probes having reporter and quencher at opposite ends of the oligonucleotide, hybridization caused a in dramatic increase in RQ.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for detecting nucleic acid target sequences in a sample comprising:

contacting a sample of nucleic acids with an oligonucleotide probe attached to a solid support under conditions favorable for hybridization, the oligonucleotide probe having a sequence at least partially complementary to a target nucleic acid sequence to be detected, the oligonucleotide probe including a fluorescent reporter molecule and a fluorescent quencher molecule capable of quenching the fluorescence of said reporter molecule, said oligonucleotide probe existing in at least one single-stranded confirmation when unhybridized where said quencher molecule quenches the fluorescence of said reporter molecule, said oligonucleotide probe existing in at least one confirmation when hybridized to said target polynucleotide where the fluorescence of said reporter molecule is unquenched, the ratio of the fluorescence intensities of said reporter molecule to said quencher molecule when said probe is hybridized to said target polynucleotide is greater than the ratio of the fluorescence intensities of said reporter molecule to said quencher molecule when said probe is single stranded; and monitoring the fluorescence of said reporter molecule, an increase in the fluorescence intensity of the reporter molecule indicating the presence of the target sequence.

2. The method according to claim 1 wherein the ratio of the fluorescence intensities of said reporter molecule to said quencher molecule when said probe is hybridized to said target polynucleofide is at least about a factor of 6 greater than the ratio of the fluorescence intensities of said reporter molecule to said quencher molecule when said probe is single-stranded.

* * * * *

UNITED STATES PATENT AND TRADEMARK OFFICE
CERTIFICATE OF CORRECTION

PATENT NO.         : 6,821,727 B1                                Page 1 of 1
APPLICATION NO. : 09/627753
DATED                 : November 23, 2004
INVENTOR(S)       : Kenneth J. Livak et al.

It is certified that error appears in the above-identified patent and that said Letters Patent is hereby corrected as shown below:

Title Page

Under Section (75) entitled, "Inventors," please replace, "Jeffrey Mamoro" with -- Jeffrey Marmaro--.

Claim 1, column 27, lines 3 and 6, please replace "confirmation" with --conformation--.

Claim 2, column 28, line 9, please replace "polynucleofie" with --polynucleotide--.

Signed and Sealed this

Twentieth Day of March, 2007

JON W. DUDAS
*Director of the United States Patent and Trademark Office*

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 24 nucleotides
      (B) TYPE: nucleic acid
      (C) STRANDEDNESS: single
      (D) TOPOLOGY: linear (xi) SEQUENCE DESCRIPTION: SEQ ID NO: 1:

ACCCACAGGA ACTGATCACC ACTC      24

(2) INFORMATION FOR SEQ ID NO: 2:

(i) SEQUENCE CHARACTERISTICS:
      (A) LENGTH: 26 nucleotides
      (B) TYPE: nucleic acid
      (C) STRANDEDNESS: single
      (D) TOPOLOGY: linear (xi) SEQUENCE DESCRIPTION: SEQ ID NO: 2:

ATGTCGCGTT CCGGCTGACG TTCTGC      26

(2) INFORMATION FOR SEQ ID NO: 3:

(i) SEQUENCE CHARACTERISTICS:
      (A) LENGTH: 27 nucleotides

```
            (B) TYPE: nucleic acid
            (C) STRANDEDNESS: single
            (D) TOPOLOGY: linear (xi) SEQUENCE DESCRIPTION: SEQ ID NO: 3:

TCGCATTACT GATCGTTGCC AACCAGT                                         27

(2) INFORMATION FOR SEQ ID NO: 4

(i) SEQUENCE CHARACTERISTICS:
            (A) LENGTH: 31 nucleotides
            (B) TYPE: nucleic acid
            (C) STRANDEDNESS: single
            (D) TOPOLOGY: linear (xi) SEQUENCE DESCRIPTION: SEQ ID NO: 4

GTACTGGTTG GCAACGATCA GTAATGCGAT G                                    31

(2) INFORMATION FOR SEQ ID NO: 5

(i) SEQUENCE CHARACTERISTICS:
            (A) LENGTH: 28 nucleotides
            (B) TYPE: nucleic acid
            (C) STRANDEDNESS: single
            (D) TOPOLOGY: linear (xi) SEQUENCE DESCRIPTION: SEQ ID NO: 5

CGGATTTGCT GGTATCTATG ACAAGGAT                                        28

(2) INFORMATION FOR SEQ ID NO: 6

(i) SEQUENCE CHARACTERISTICS:
            (A) LENGTH: 31 nucleotides
            (B) TYPE: nucleic acid
            (C) STRANDEDNESS: single
            (D) TOPOLOGY: linear (xi) SEQUENCE DESCRIPTION: SEQ ID NO: 6

TTCATCCTTG TCATAGATAC CAGCAAATCC G                                    31

(2) INFORMATION FOR SEQ ID NO: 7

(i) SEQUENCE CHARACTERISTICS:
            (A) LENGTH: 25  nucleotides
            (B) TYPE: nucleic acid
            (C) STRANDEDNESS: single
            (D) TOPOLOGY: linear (xi) SEQUENCE DESCRIPTION: SEQ ID NO: 7

TCACCCACAC TGTGCCCATC TACGA                                           25

(2) INFORMATION FOR SEQ ID NO: 8

(i) SEQUENCE CHARACTERISTICS:
            (A) LENGTH: 25 nucleotides
            (B) TYPE: nucleic acid
            (C) STRANDEDNESS: single
            (D) TOPOLOGY: linear (xi) SEQUENCE DESCRIPTION: SEQ ID NO: 8

CAGCGGAACC GCTCATTGCC AATGG                                           25

(2) INFORMATION FOR SEQ ID NO: 9

(i) SEQUENCE CHARACTERISTICS:
            (A) LENGTH: 26 nucleotides
            (B) TYPE: nucleic acid
```

-continued (C) STRANDEDNESS: single
        (D) TOPOLOGY: linear (xi) SEQUENCE DESCRIPTION: SEQ ID NO: 9

ATGCCCTCCC CCATGCCATC CTGCGT                                    26

(2) INFORMATION FOR SEQ ID NO: 10

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO: 10

AGACGCAGGA TGGCATGGGG GAGGGCATAC                                30

(2) INFORMATION FOR SEQ ID NO: 11

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (xi) SEQUENCE DESCRIPTION: SEQ ID NO: 11

CGCCCTGGAC TTCGAGCAAG AGAT                                      24

(2) INFORMATION FOR SEQ ID NO: 12

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (xi) SEQUENCE DESCRIPTION: SEQ ID NO: 12

CCATCTCTTG CTCGAAGTCC AGGGCGAC                                  28

(2) INFORMATION FOR SEQ ID NO: 13

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 13

CAAGCTTCCC GTTCTCAGCC T                                         21

(2) INFORMATION FOR SEQ ID NO: 14

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO: 14

ACCGTCAAGG CTGAGAACGG GAAGCTTGTC                                30